United States Patent
Harden et al.

(10) Patent No.: US 7,468,672 B2
(45) Date of Patent: Dec. 23, 2008

(54) DETECTION AND IDENTIFICATION METHOD FOR IN-TRANSIT DETERMINATION OF CHEMICAL CONTRABAND, DECAYING ANIMAL AND VEGETABLE MATTER, AND CONCEALED HUMANS IN CARGO SHIPPING CONTAINERS AND OTHER SECURE SPACES

(75) Inventors: Charles S. Harden, 509 W. Ring Factory Rd., Bel Air, MD (US) 21015; Joseph C. Harden, Hilton Head Island, SC (US)

(73) Assignee: Charles S. Harden, Bel Air, MD (US)

( * ) Notice: Subject to any disclaimer, the term of this patent is extended or adjusted under 35 U.S.C. 154(b) by 245 days.

(21) Appl. No.: 11/443,950

(22) Filed: May 31, 2006

(65) Prior Publication Data
US 2007/0277589 A1 Dec. 6, 2007

(51) Int. Cl.
*G08B 23/00* (2006.01)

(52) U.S. Cl. .................................... 340/573.1

(58) Field of Classification Search .............. 340/573.1, 340/573.4, 539.11–539.13, 632–634, 612; 73/23.2–23.22, 23.34–23.37, 31.05–31.06, 73/35.16; 702/19–32
See application file for complete search history.

(56) References Cited

U.S. PATENT DOCUMENTS

| | | | |
|---|---|---|---|
| 4,987,767 A * | 1/1991 | Corrigan et al. ............ 73/23.36 |
| 5,162,652 A | 11/1992 | Cohen et al. ................. 250/288 |
| 5,345,809 A * | 9/1994 | Corrigan et al. .............. 73/23.2 |
| 6,252,510 B1 * | 6/2001 | Dungan ....................... 340/632 |
| 6,502,470 B1 | 1/2003 | Taylor et al. ............. 73/864.35 |
| 6,773,674 B2 * | 8/2004 | Bannister et al. .............. 422/83 |
| 6,794,645 B2 | 9/2004 | Kanik et al. ................. 250/288 |
| 6,823,714 B2 * | 11/2004 | Megerle ...................... 73/23.2 |
| 6,837,096 B2 * | 1/2005 | Stewart ...................... 73/23.35 |
| 7,062,385 B2 * | 6/2006 | White et al. ................... 702/23 |

(Continued)

OTHER PUBLICATIONS

P. Lafontaine et al, "The Use of GC-IMS to Analyze High Volume Vapor Samples from Cargo Containers"; 9th International Conference on Ion Mobility Spectrometry, Aug. 13-16, 2000.

(Continued)

*Primary Examiner*—George A Bugg
*Assistant Examiner*—Samuel J Walk
(74) *Attorney, Agent, or Firm*—Hodes, Pessin & Katz, P.A.

(57) ABSTRACT

A chemical analysis method for detecting, identifying and reporting contraband, illegal drugs, explosives, toxic chemicals, decaying animal and vegetable matter, and concealed human beings located in secure spaces such as cargo shipping containers. Chemical analysis results are accumulated and added to effect definitive analyses over extended periods of time while the containers are in transit. Individual containers are equipped with a device employing the method. The analysis method consists of accumulation and addition of analytical chemical instrumentation, measurements of trace quantities of target chemical vapors inside of shipping containers while the containers are in transit. Cumulative and additive spectrometric analyses coupled with increased target chemical concentrations, due to chemical vapor build up over the long periods of time that containers are in transit, result in significantly increased electronic signal-to-noise in spectrometric measurements and increased spectrometric signal strengths that are indicative of the presence of target chemicals.

15 Claims, 7 Drawing Sheets

U.S. PATENT DOCUMENTS

| | | | |
|---|---|---|---|
| 7,100,424 B2 * | 9/2006 | Wilson | 73/31.05 |
| 7,158,028 B1 * | 1/2007 | Ghahramani | 340/539.22 |
| 7,229,821 B1 * | 6/2007 | Edmonson et al. | 435/287.1 |
| 2005/0022581 A1 | 2/2005 | Sunshine | 73/31.05 |
| 2006/0156792 A1 * | 7/2006 | Wang | 73/23.37 |
| 2006/0266102 A1 * | 11/2006 | Tolliver | 73/23.2 |

OTHER PUBLICATIONS

I. A. Buryakov et al, "A New Method of Separation of Multi-atomic Ions by Mobility at Atmospheric Pressure Using High-Frequency Amplitude-Asymmetric Strong Electric Field"; International Journal of Mass Spectrometry and Ion Processes 128 (1993) pp. 143-148.

* cited by examiner

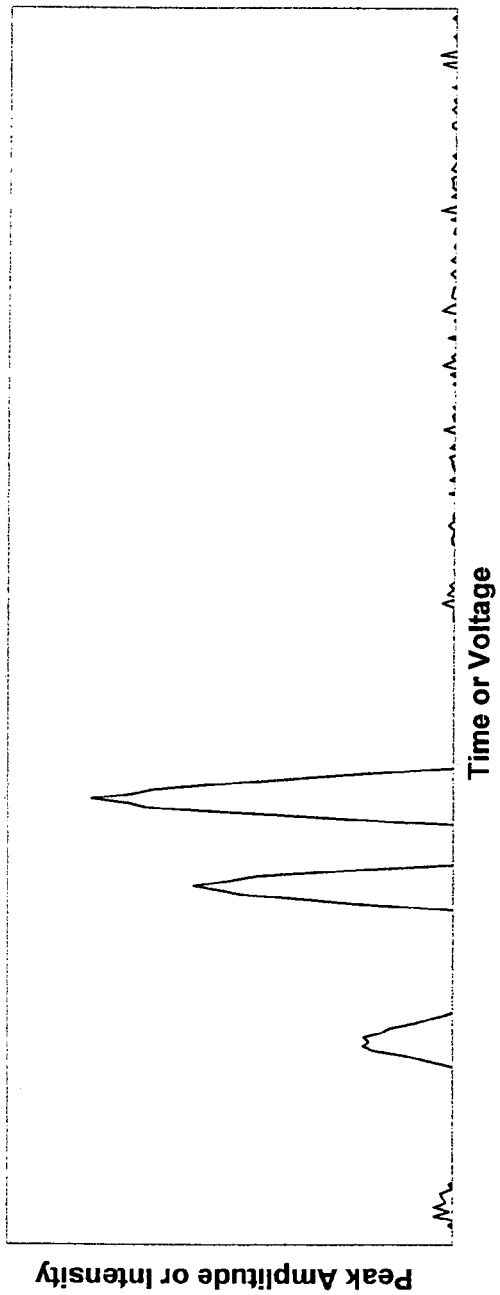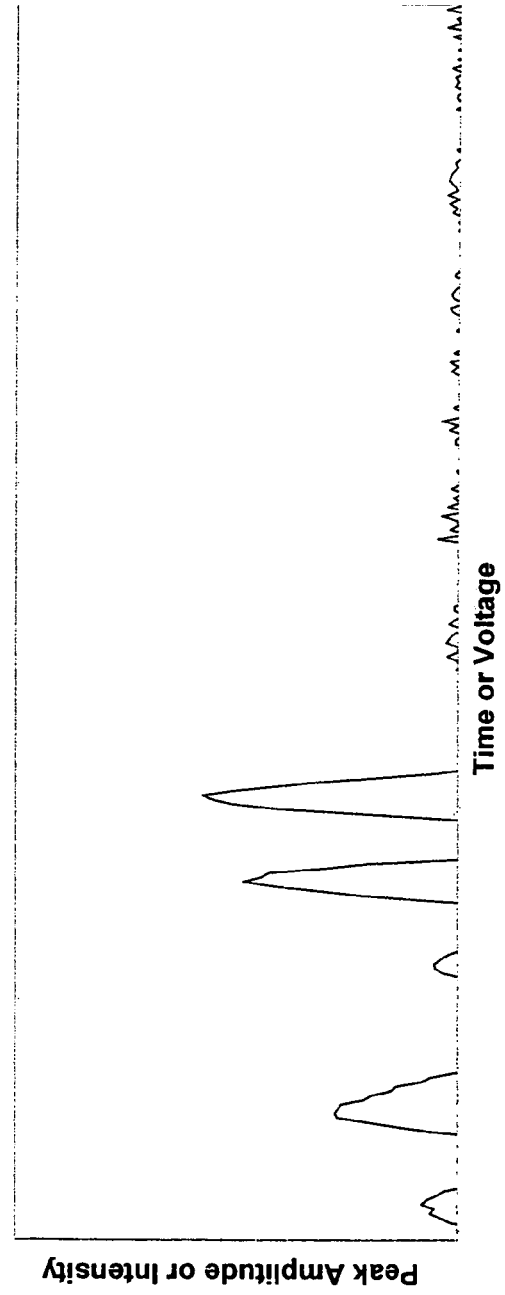

DETECTION AND IDENTIFICATION METHOD FOR IN-TRANSIT DETERMINATION OF CHEMICAL CONTRABAND, DECAYING ANIMAL AND VEGETABLE MATTER, AND CONCEALED HUMANS IN CARGO SHIPPING CONTAINERS AND OTHER SECURE SPACES

BACKGROUND OF THE INVENTION

1. Field of the Invention

The invention is a method of chemical analysis for detecting and reporting contraband such as illicit and illegal drugs, explosives, toxic chemicals, decaying animal and vegetable matter, and concealed human beings located in confined spaces of shipping containers and other cargo containers and secure spaces. The chemical analyses take place periodically while the containers are in transit from the time that the containers are stuffed and sealed, to the time when the containers move through inspection chokepoints, through the shipping time of the containers, and to the time that the containers are inspected at national border crossing points. During the transit time concentrations of chemical vapors of the materials to be detected, i.e., the target chemicals, increase by diffusing out of packaging into and throughout the container. The periodic chemical analyses are added together which has the effect of emphasizing responses of the analysis to chemicals that are increasing in concentration or that have reached a steady-state concentration while averaging out or de-emphasizing responses to chemicals that fluctuate in concentration. In addition, signal processing enhancement of spectra, for example, spectral deconvolution, can be employed during the extensive analysis time available while the containers are in transit. Total analysis time ranges from a few hours to several days.

2. Description of Related Art

At the present time, there are no methods or procedures for monitoring the contents of shipping containers, storage containers or other cargo containers by having a detector within the container. When such a container arrives at its destination, a statistical number of containers are randomly tested by sampling the exhaust vent of the container for a selected type of target chemical. The test does not include all types of potential contaminants. Further, due to time and cost constraints, the sampling time is relatively short and may not be a representative sample of the contents of the container.

Ion mobility spectrometry (IMS) devices for detection of contraband, drugs and explosives, are commonly used by inspection personnel at security chokepoints in airports, seaports, and border crossings throughout the world. IMS devices for detection of chemical warfare agents are used worldwide by military, law enforcement, and security personnel to detect and prevent exposure to lethal and incapacitating chemicals. However, current applications of IMS detection devices, or other analytical chemical instruments, require high speed of response to prevent bottlenecks at security chokepoints and to detect toxic chemicals before the chemicals are ingested by people in sufficient quantities to be physiologically dangerous. In every previous method and application of analytical chemical instrumentation, analyses of atmospheres for contraband or dangerous materials, minimization of response time has been emphasized. Many of the detection systems require human operators who acquire samples, introduce samples into the detector, and monitor detector results.

There are no known methods or applications of analytical chemical detection instrumentation, for example IMS devices, for accumulation and addition of chemical detection data inside of shipping containers while the containers are in transit for the purpose of detecting and reporting decaying animal and vegetable matter. There are no known methods or applications of analytical chemical detection instrumentation, for example IMS devices, for accumulation and addition of chemical detection data inside of shipping containers while the containers are in transit for the purpose of detecting body effluvia from concealed human beings although it is common knowledge in the analytical chemistry field that human effluvia such as ammonia, carbon dioxide, sulfides, volatile organic acids, amines and diamines are readily detectable by IMS.

IMS technology and devices based on IMS technology have been developed for detection of drugs and explosives. One example of detection systems for drugs and explosives is the detectors at airport security check-in locations. The operator of one of these devices must rub a swab over a piece of luggage and then place the swab in an instrument to determine whether there are certain chemicals on the bag, i.e., chemicals that have been transferred to the bag due to previous handling of the contraband. Emphasis is on speed of response but this process requires a few minutes and operator intervention and is impractical for use on every passenger passing through an airport. Similar instruments have been proposed for use by Customs inspectors who attach them to vents of shipping container, a process requiring several tens of minutes to an hour making it impractical to examine every container passing through seaports. These detection instruments are designed to detect either drugs or explosives but not both at the same time—the instruments must be reprogrammed from detection of one form of contraband to detection of another form of contraband.

There are millions of shipping containers and cargo carriers in use in the world and many more millions of container and carrier uses per year. Inspection of cargo containers and carriers is time consuming and results in delays in timely movement of containers across national border crossing, through seaports, and through airports. A detailed inspection of a single cargo container for contraband substances can take hours to accomplish. Speeding of the inspection capability is a prime interest of governments around the world to provide timely and efficient interdiction. The method described in the present patent application will facilitate the inspection process by indications of containers that are likely to contain contraband or to indicate containers that need not be inspected.

The present invention pertains to a method of chemical analysis for detecting and reporting contraband and not the detection device. A small, unobtrusive, low power consumption device is pertinent from a practical point of view because of limited space available in packed shipping containers and because of the need to perform chemical analyses over periods of several hours to several days. The present invention is for chemical analysis to take place while cargo containers are in transit from the time that the containers are stuffed, to the time when the containers move through inspection chokepoints, through the shipping time of the containers, and on to the time that the containers are inspected at national border crossing points. This is in contrast to requirements for rapid response of detection instrumentation that is currently employed for inspecting cargo containers at transportation chokepoints. The present invention relies on the fact that the total time available for employing the method of analysis ranges from a few hours to several days.

In Publication US 2005/0022581, Sunshine discloses a chemical sensing system having an interrogation unit to wirelessly transmit an interrogation signal and to wirelessly receive a response. Various sensors are disclosed, none of which are IMS. Also, a sample is introduced into a container, the sample having a relationship with an analyte in the container which is detected by the sensor.

The use of a gas chromatograph—IMS device to analyze high volume vapor samples from cargo containers is reported by La Fontaine in the 9$^{th}$ International Conference on Ion Mobility Spectrometry, Aug. 13-16, 2000.

Thus, there is a need for a method which can detect the presence of target chemicals in confined spaces such as cargo shipping containers as the containers are in transit and concentrations of the target materials accumulate over a period of time. There is a further need to move the shipping containers rapidly through the transportation choke points.

SUMMARY OF THE INVENTION

In the present invention, rapid chemical analysis is neither required nor is rapid chemical analysis desirable. The present invention makes use of the advantage of long term analysis times being available for chemical analyses during transit of containers, analysis times of a few hours to several days. The long term transit times of cargo containers are utilized 1) to allow accumulation of concentrations of contraband vapors in the enclosed spaces to concentrations that are more reliably detectable and 2) to improve sensitivity and specificity of the analysis process by continuously adding sequential responses to analyses instruments, i.e., signal averaging, at intervals, throughout the in-transit analysis time. Preferably, the fact that the concentrations of contraband are building up will be used in the detection algorithm as a part of the contraband vapor identification process. Utilization of the significant amounts of time that containers are in transit to allow build up of contraband vapors and to allow for cumulative and additive analytical instrument analyses is the uniqueness of the present invention for detection of contraband, decaying animal and vegetable matter, and concealed humans. Longer times for processing chemical samples and analyzing chemical detector data will result in more effective detections and repressions of false detections.

In accordance with the teachings of the present invention, there is disclosed a method for detection and identification of illegal drugs, explosives, toxic chemicals, decaying animal and vegetable matter, and concealed human beings located in confined spaces of shipping containers, storage containers and other cargo containers and secure spaces. The method provides an analytical chemical detector which has low power requirements and is powered by a battery to operate a detector and to sample the atmosphere within the confined spaces. The analytical chemical detector is disposed in said confined spaces for a period of time wherein there is an accumulation of target chemicals associated with the illegal drugs, explosives, toxic chemicals, decaying animal and vegetable matter, and/or human effluvia. The analytical chemical detector is sensitive to minute concentrations of the target chemicals. A means is provided for accumulating, adding and processing chemical analysis measurements periodically over said period of time as the target chemicals accumulate to significant concentration in said confined spaces. Digital signal processing algorithms are provided to identify the target chemicals. A means is provided for reporting the presence of the target chemicals to a device located outside of the confined spaces.

These and other objects of the present invention will become apparent from a reading of the following specification taken in conjunction with the enclosed drawings.

BRIEF DESCRIPTION OF THE DRAWINGS

FIG. 3A is a typical spectrum of cocaine produced by the detector.

FIG. 3B is a typical spectrum of cocaine detected in a container.

DESCRIPTION OF THE PREFERRED EMBODIMENTS

Chemical contraband materials 34 packaged inside a shipping container 30 exude small amounts of the actual contraband chemical or chemicals associated with the contraband such as precursor chemicals, decomposition products or taggants. From a practical point of view, it is not possible to completely seal a package so that none of the chemicals escape the package. In actuality, minute amounts of the chemicals escape into the atmosphere of the container. Over time, the chemicals will diffuse throughout the container and concentrations of the chemicals will build up.

Figure 1A:
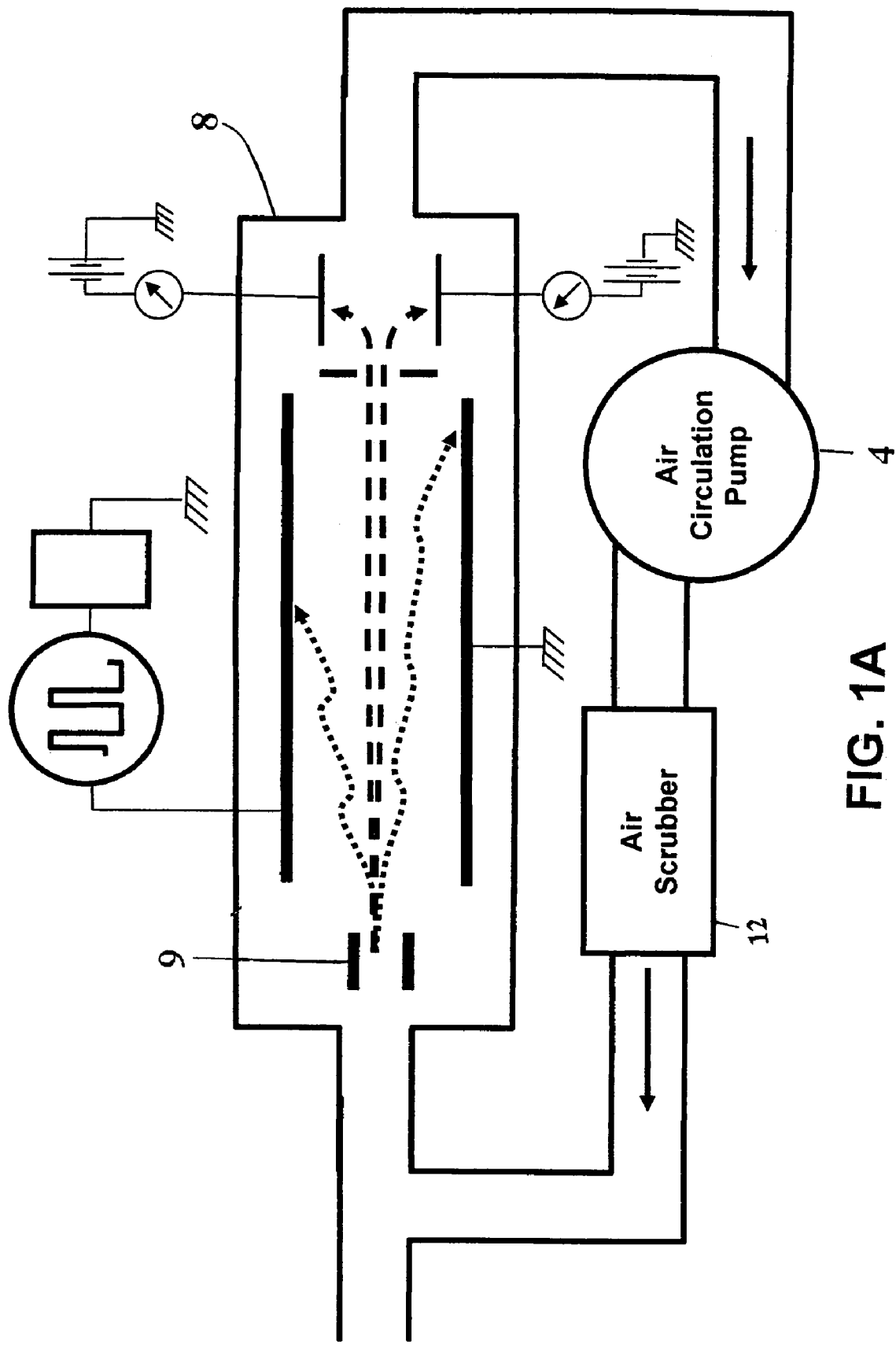
FIG. 1A is a schematic diagram of one type of ion mobility spectrometer.

Technology exists in the form of small, low-power-consumption, hand-held chemical detectors that have been developed for detection of and protection of war fighters from weapons of mass destruction (WMD). The technology, Ion Mobility Spectrometry (IMS), has been in use by worldwide military services for at least 20 years. The technology is routinely used by law enforcement and security personnel in searching for concealed contraband (drugs and explosives). Small, unobtrusive, low electrical power consumption devices have been developed and are commercially available. One such device is being manufactured and distributed and is based on previous inventions (Taylor et al, U.S. Pat. No. 6,512,470). This device relies on analyses of ions in uniform and linear electric fields, the ions indicating presence of target chemicals contain electrically charged species, for example protons, protonated molecules, oxygen ions, and molecules of the target chemicals. A second device is based on technology that was initially reported in 1993 (Buryakov et al). In typical devices based on this method of ion separation, an air circulation pump (4) moves air through a scrubber to provide for clean air to be mixed with incoming sample laden air (FIG. 1A). The sample air mixed with clean air passes through a source of ionization (9), through the analytical region, past ion current collectors and on to the circulation pump. Ions containing molecules of contraband materials or materials associated with contraband are formed in the ion source. These ions are dragged along with the flowing air through the analytical region. The analytical region consists of the gap between parallel plate electrodes or concentric cylinder electrodes. One of the electrodes is held at ground potential. On the other electrode, high amplitude, high frequency, asymmetric waveform voltage which is superimposed on a variable direct current (DC) voltage is applied. The effect of the asymmetric waveform voltage is to cause the ions to drift toward one of the electrodes or the other. The DC voltage causes ions to drift toward the opposite electrode. For a given ionic species, ion mobility characteristics are unique and the combination of asymmetric waveform voltage and DC voltage that allows such ions to pass completely through the analytical region, i.e., ionic species whose trajectories are stable, is unique. Both positive and negative ions may pass through the analytical region at the same time and ions whose trajectories are stable are measured as ion current by one or the other of the ion collectors. Ions whose trajectories are unstable collide with one of the electrodes before passing completely through the analytical region and are annihilated. For an ion mobility spectrometric measurement the amplitude and frequency of the asymmetric waveform voltage would be held constant and the DC voltage varied. For subsequent ion mobility spectrometric measurements the value of the amplitude of the asymmetric waveform voltage could be changed to another value while the frequency would be held constant and the DC voltage varied. It would be possible to vary the frequency of the asymmetric waveform voltage but this is not common. Various combinations of asymmetric waveform voltage and DC voltages are commonly used to generate ion mobility spectrometric measurements. An ion mobility spectrum resulting from a device based on the concept of Buryakov et al is a plot of the intensity of measured ion current versus the magnitude and polarity of the DC voltage. The present invention as disclosed herein utilizes IMS as the detection principle but is not so limited. Any detector known to persons skilled in the art may be used if it has the requisite sensitivity to the target chemicals and can operate unattended with very low power requirements.

Figure 1B:
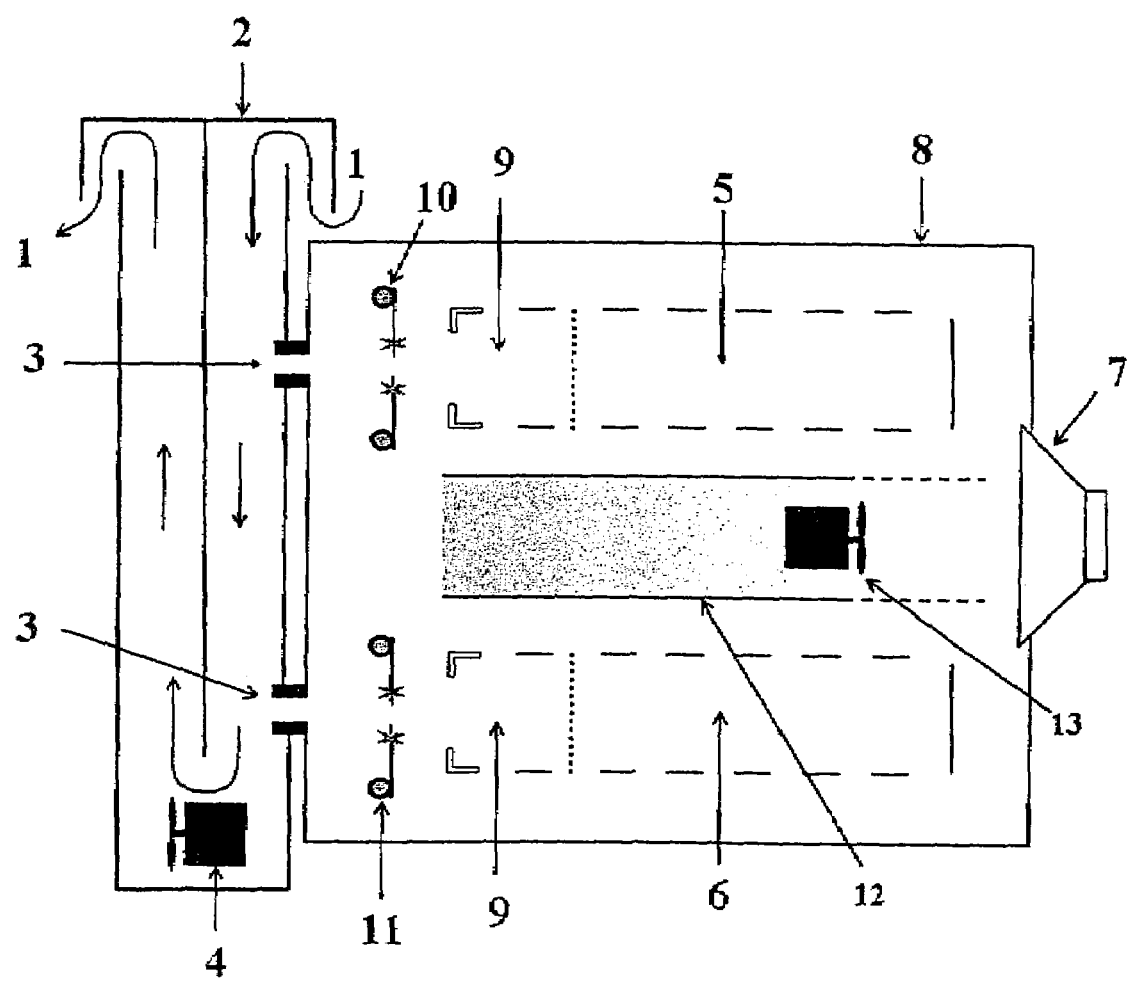
FIG. 1B is a schematic diagram of another type of ion mobility spectrometer.

In order to better understand the IMS, FIG. 1B is a schematic diagram of another typical ion mobility spectrometer. In the device sample laden air (1) flows through a plenum (2) over two pinholes (3) by means of a small blower (4). Periodically, under control of an on-board microprocessor, small samples of ambient air are ingested through the pinholes (3) into each of two ion mobility spectrometers (5), (6) using a small pulsed loudspeaker (7) attached to the housing (8) of two ion mobility spectrometers (5), (6). One ion mobility spectrometer (5) is used for analysis of positive ions; the other (6) is used for analysis of negative ions. As the diaphragm of the loudspeaker (7) is electronically pulsed and moves away from the housing (8) pressure is momentarily decreased inside the housing (8) and small "puffs" of sample laden air enter through the pinholes (3) directly into the ionization region (9) of each of the ion mobility spectrometers (5), (6). While the samples are in the ionization regions (9), pulsed electrical discharges (10), (11) are activated in each of the ion mobility spectrometers (5), (6) producing corona discharge ionizing pulses (10), (11); a positive ion corona discharge (10) produces ions in the positively biased spectrometer (5) and a negative ion corona discharge (11) produces ions in the negatively biased spectrometer (6). Ion mobility spectra are acquired in each of the ion mobility spectrometers in a manner similar to that described in U.S. Pat. No. 5,162,652 (Cohen, 1992) and U.S. Pat. No. 6,794,645 (Kanik, 2004)—spectra of ions representative of chemicals in the air sample are generated in each ion mobility spectrometer. Spectra are generated for positive and negative ions simultaneously. The reaction regions (9) of the two ion mobility spectrometers (5), (6) must be purged with clean air after introduction of each sample in order to provide for independent samples to be ingested into and ionized in the corona discharge regions (10), (11). The purging allows independent IMS analyses to be obtained for each sample. Purging is accomplished by recirculating air inside the device through an air scrubber (12) by means of an internal blower (13).

The following five paragraphs contain partial listings of chemicals that are readily detected by IMS and other analytical chemical instrumentation. The partial listing is of chemicals that increase in concentration over extended periods of time in confined spaces and chemicals for which extended analysis times result in improved and more reliable detection and identification. The lists are intended to demonstrate the kinds of chemicals that are detectable within the scope of the present invention. The fact that a chemical may not be listed does not mean that analysis and detection of the omitted chemical is outside of the scope of the present invention.

(1) Illegal drugs and chemicals related to illegal drugs detected by IMS and related analytical chemical instrumentation include but are not limited to illegal drugs such as cocaine, heroin, methamphetamine, marijuana. Chemicals related to manufacture of illegal drugs detected by IMS include but are not limited to anthranilic acid, its esters and salts; ephedrine, its salts, optical isomers, and salts of optical isomers; phenylacetic acid, its esters, and its salts; phenylpropanol amine, its salts, optical isomers; methyl amine; ethyl amine; propionic anhydride; hydriodic acid; benzaldehyde; nitroethane; gamma butyroacetone. Additional chemicals related to manufacture of illegal drugs that are detected by IMS and related analytical chemical instrumentation include but are not limited to acetic anhydride; acetone; ethyl ether; methyl ethyl ketone; toluene; iodine, hydrochloric gas.

(2) Explosives detected by IMS and related analytical chemical instrumentation include but are not limited to explosives such as: 2,4,6-trinitrotoluene (TNT); 2,4,6-trinitroamine (RDX), pentaerythritol tetranitrate (PETN), ethylene glycol dinitrate (EGDN). Since 1996 explosives manufactured or imported into the United States must contain detection agents or taggants—taggants include 2,4-dinitrotoluene (DNT); ethylene glycol dinitrate (EGDN); 2,3-dimethyl-2,3-dinitrobutane (DMDB); para-mononitrotoluene (p-MNT); ortho-mononitrotoluene (o-MNT).

(3) Chemical weapons of mass destruction and precursors used in synthesis of such compounds detected by IMS and related analytical chemical instrumentation include but are not limited to nerve agents such as ethyl N,N-dimethylphosphoroamidocyanidate (Tabun or GA), isopropyl methyl phosphonofluoridate (Sarin or GB), pinacolyl methyl phosphonofluoridate (Soman or GD), cyclohexyl methyl phosphonofluoridate (GF), O-ethyl-S-(2-isopropylaminoethyl)methyl phosphonothiolate (VX); Blister agents: bis-2-chloroethyl sulfide (Mustard Gas or HD), tris-2-chloroethyl amine (Nitrogen Mustard, HN3), dichloro-(2-chlorovinyl)arsine (Lewisite or L); Blood agents: hydrogen cyanide (AC), cyanogen chloride (CK); Choking agents: carbonyl chloride (CK). Precursors detected by IMS include di-isopropyl methyl phosphonate (DIMP); methyl phosphonic difluoride (DF), methyl phosphonic dichloride (DICL), bis-hydroxyethyl sulfide.

(4) Chemicals detected by IMS and related analytical chemical instrumentation and chemical that are related to decaying animal and vegetable matter include but are not limited to primary, secondary and tertiary aliphatic amines; α-ω-alkyl diamines, particularly cadaverine and putricine.

(5) Human effluvia detected by IMS and related analytical chemical instrumentation include but are not limited to: ammonia, carbon dioxide, alkyl sulfides, volatile organic acids, α-ω-alkyl diamines.

Figure 2:
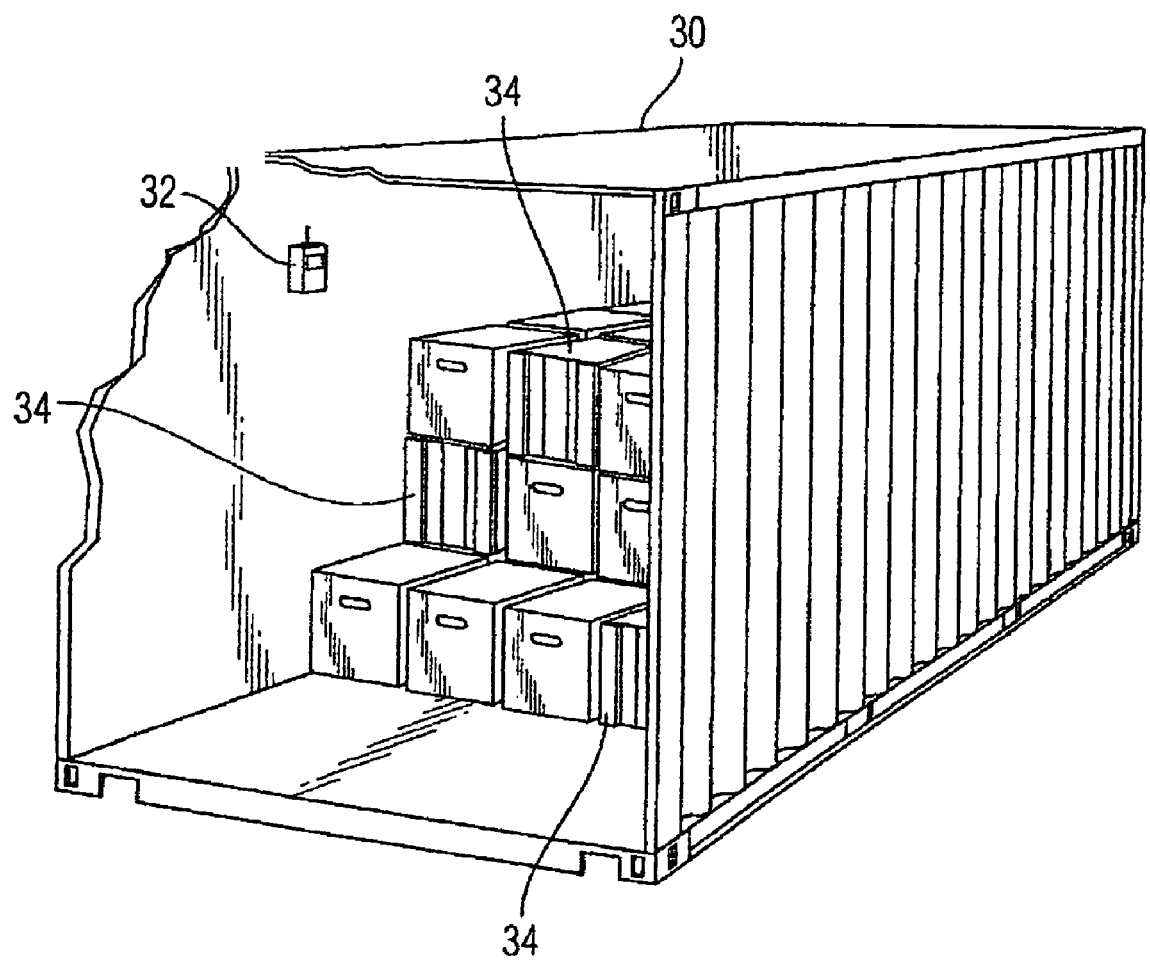
FIG. 2 is a cutaway perspective view of a shipping container loaded with cargo with the detector of the present invention disposed within the container.

The basis for the present invention is to perform periodic, cumulative and additive chemical analyses of the inside air of containers and to perform the analyses for extended periods of time during the time in which the containers are in transit (FIG. 2). Rapid response time is not required. The devices 32 to be used in the present invention are small, unobtrusive, sensitive, and consume little electrical power. Preferably, the devices should be able to operate for tens of hours on standard, readily available, batteries. Detection devices 32 to be used in the present invention are contrasted with other detection devices, such as detection devices based on IMS technology that have been developed for detection of drugs and contraband and to military instrumentation for detection of chemical warfare materials. Such existing units are relatively large, consume large amounts of electrical power, and some require human operators. Inspectors using state-of-the-art instrumentation for contraband detection by security personnel at airports, seaports, and border crossings require significant amounts of time, require human operators, and cost on the order of $20,000 or more each. The expected costs of instruments for the present invention is expected to be on the order of $2,000 to $3,000 with service lifetimes of more than five years.

Airborne concentrations of contraband 34 in containers 30 will almost always be very small. In chemical analysis terms this translates to a requirement for extensive amounts of sample processing time for an analysis or employment of a method to concentrate the sample before analysis. Time consuming analyses at transportation chokepoints precludes rapid and effective inspection of cargo containers and result in slow movement of cargo across national borders. During the time that a shipping container is in transit, there is sufficient time to perform the analytical chemical analyses of the present invention with or without resorting to use of pre-concentration techniques. The present invention performs the analyses while the container is in transit and to perform the analyses automatically, cheaply, and reliably without expenditure of extensive amounts of electrical power.

Figure 4:
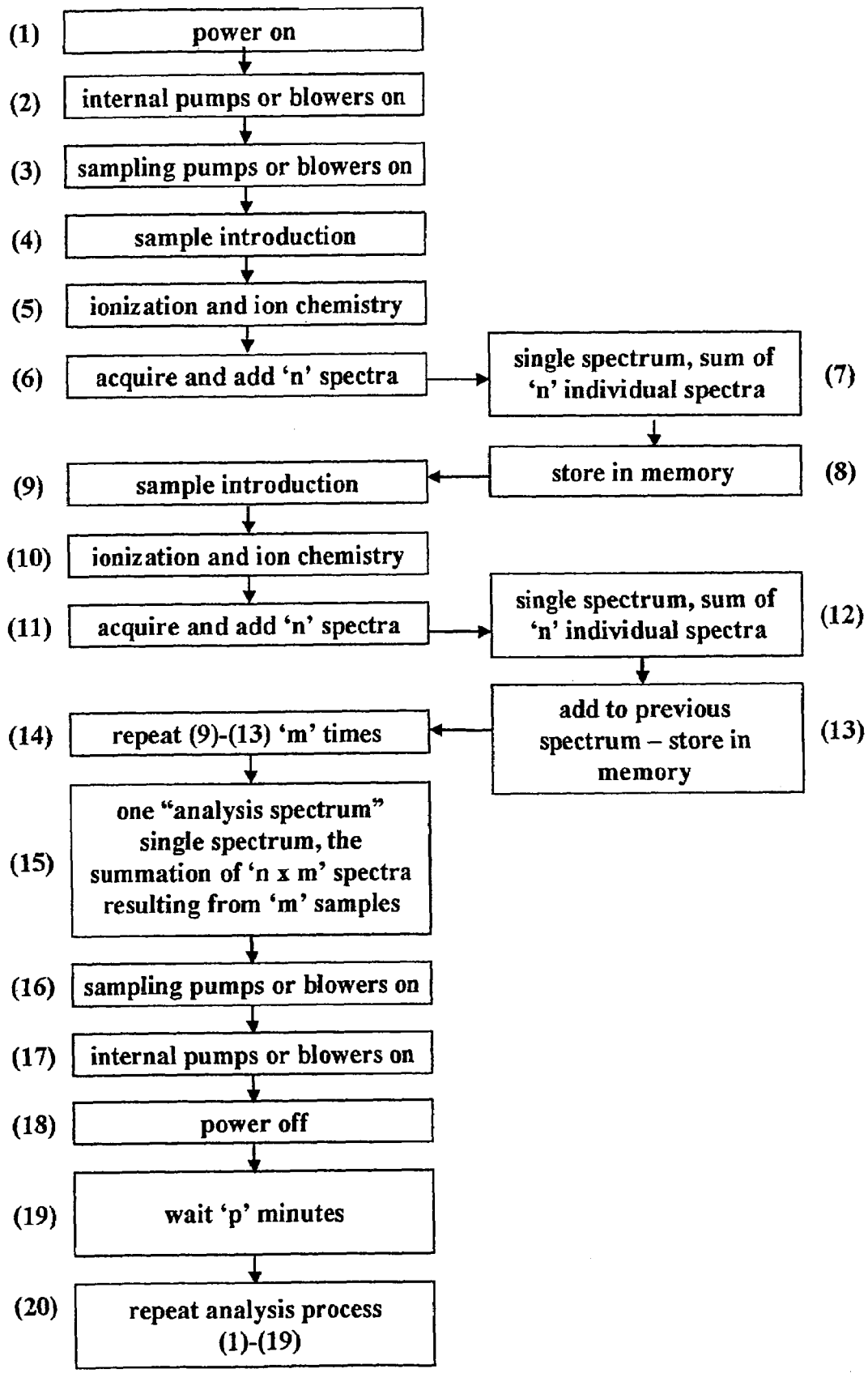
FIG. 4 is a flow diagram of the method of analysis.

FIG. 4 is a flow diagram showing acquisition of a single analysis referred to herein as an analysis spectrum. One analysis spectrum could consist of up to several hundred co-added individual measurements or individual spectra. One analysis spectrum is acquired at intervals of several minutes to several hours. A typical operation consists of the following steps: (1) the device is powered up; (2) an internal pump or blower is turned on to begin to clear the detector of chemicals that might have diffused into the device during periods of inactivity; (3) a sampling pump or blower is turned on to ingest an air sample into the detector; (4) the air sample that is representative of air inside the container is moved into the analysis volume of the detector; (5) in the case of ion mobility spectrometers, the air sample is moved into the ionization and reaction region; (6) a number "n" of individual analytical measurements or spectra are acquired and co-added, typically 8 to 16 measurements will be acquired and co-added; (7) a single measurement or spectrum that is the sum of "n" individual measurements or spectra is produced; (8) a single measurement or spectrum is stored in detector memory. A number "m" of successive measurements or spectra are co-added increase electronic signal-to-noise ratio; (9)-(14) the sample introduction, ionization and ion chemistry, acquisition and addition of "n" single measurements or spectra storing the resulting measurement or spectrum in detector memory is repeated "m" times; (15) the process of acquiring and accumulating n×m measurements or spectra results in one analysis measurement or analysis spectrum that consists of n×m individual, co-added or signal-averaged measurement or spectrum. The values of "n" and "m" are dependent on the nature of the target chemical. Typically, a value of "n" might be 8 to 16 and a typical value of "m" might be 25 resulting in "analysis measurement" or "analysis spectrum" consisting of 200 to 400 individual measurements or spectra. Addition of the individual analytical measurements or spectra improves electronic signal-to-noise and averages out measurement or spectral features that arise from chemicals that are rapidly fluctuating in concentration. Ion mobility spectral features due to those chemicals that are increasing in concentration with time or that have reached a steady state concentration are emphasized. (16) Upon acquisition of analysis measurements or spectra, the sampling pumps or blowers are turned off; (17) the internal pumps or blowers are turned off, and (18) the power is turned to a stand-by level; (19) after a period "p" of several minutes to several hours, the process is repeated; (20) another measurement or spectrum is stored in detector memory. As an example, the total time to acquire an analysis measurement or analysis spectrum as outlined in steps 1-18 might typically be 20 minutes and step 19 might typically be 6 hours. This means that the detector power is off for approximately 95% of the time resulting in significant electrical power savings. In some applications the rate of acquisition of analysis spectra could be increased or decreased.

The target chemicals can be detected at nanogram to microgram quantities. Successive analysis measurements or analysis spectra are added to allow peaks of chemical species entrained in sample air to grow. The electrical output signals of some chemical detection instruments, including ion mobility spectrometers, are in the form of a series of peaks that are representative of chemical or physical properties measured by that instrument. When instrument signals result in two or more overlapping peaks the widely used signal processing technique of deconvolution may be employed to mathematically treat the instrument output data to produce peaks that are separate individual peaks. This process significantly aids the chemical analysis for identification of contraband and related chemicals.

FIG. 3A is an ion mobility spectrum of chemicals associated with a cocaine sample. An IMS detector was placed in close proximity to the cocaine sample and vapors emanating from the cocaine sample were measured. The ion mobility spectrum in FIG. 3A is the deconvolved sum of 800 individual ion mobility spectrometry measurements taken over a period of 500 seconds. FIG. 3B is an ion mobility spectrum of chemicals associated with a cocaine sample inside a shipping container. An IMS detector was placed in the upper headspace of a container, the cocaine sample was on the floor of the container, and the container was loaded with cardboard boxes. The ion mobility spectrum of FIG. 3B is the deconvolved sum of 1,600 individual ion mobility spectra measurements of the container atmosphere taken over a period of 1,000 seconds after the cocaine had been sealed in the container for a period of approximately 96 hours. A typical spectrum of cocaine is shown in FIG. 3A. The spectrum of cocaine taken within a container is show in FIG. 3B. If the concentration of a contraband chemical increases, as it will during the transit time of the container, detector responses due to those chemicals will increase in amplitude as successive measurements or spectra are added together. The summed measurements or spectra will be digitally compared to stored libraries of detector responses to target chemicals to identify the target chemicals. Addition of measurements or spectra will continue during the period that the container is being transported. By adding measurements or spectra over extended periods of time detections of chemicals due to random fluctuations of background chemical vapors will be averaged out. Measurements or spectra from those vapors that are steadily increasing in concentration or stable in concentration, i.e., vapors from concealed contraband, will be recorded and emphasized over spectra of vapors from fluctuating chemical concentrations. Over periods of hours to days, vapor concentrations of target chemicals will continue to increase or will reach a steady state concentration.

Figure 5:
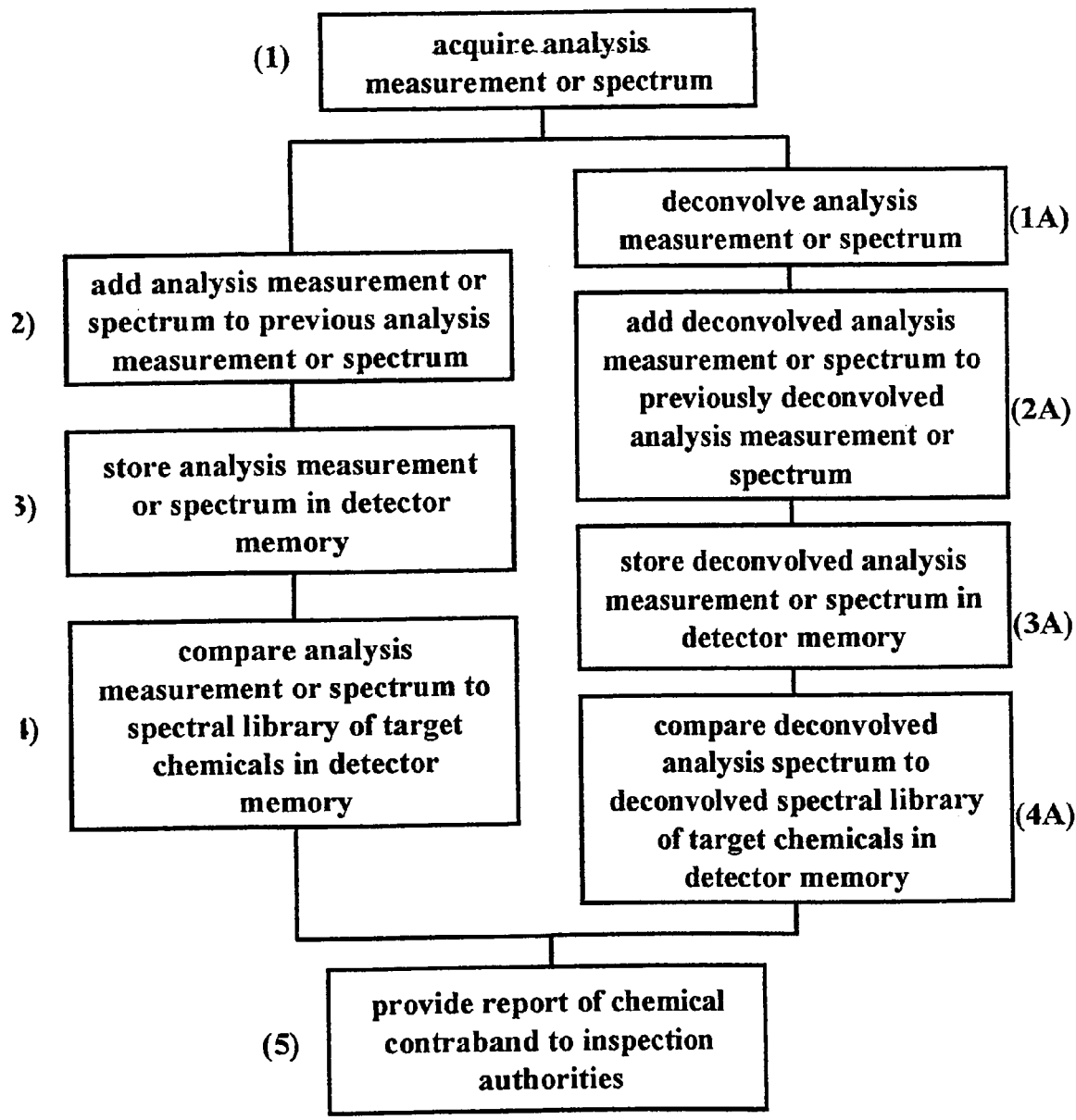
FIG. 5 is a flow diagram showing methods of manipulation of an ion mobility analysis spectrum to report on the presence of a target chemical.

There are at least two methods of manipulating the analysis spectra to test for presence of target chemicals—both methods lead to the same result. A description of these two methods is given below with the understanding that the present invention is not limited to either of the methods but may be a method known to persons skilled in the art. A flow diagram of the methods is shown in FIG. 5. The first method is to acquire an analysis measurement or analysis spectrum (1), add the analysis measurement of analysis spectrum to the previous analysis measurement or analysis spectrum (2), store the resultant measurement or analysis spectrum in memory (3), compare the resultant measurement or analysis spectrum to measurement or analysis spectral libraries (4), and provide a report of detection and identification of target chemicals (5). This method works well when detector responses due to target chemicals are spectral in nature, that is, peak producing, are relatively intense and are separated from peaks due to chemicals of no interest. The first method must be used if the detection method is not spectral in nature and responses are series of unresolved responses of, for example, arrays of chemical detection transducers. The second method is invoked only when detector response are spectral in nature and spectra peak positions are reproducible from measurement to measurement. The second method is invoked when, in some cases, target chemical peaks might be partially obscured by peaks due to chemicals of no interest. In the second method an analysis spectrum is acquired (1), the analysis spectrum is deconvolved (1A), added to the previous deconvolved analysis spectrum (2B), the resultant deconvolved analysis spectrum is stored in memory (3A), compared to libraries of deconvolved spectra (4A), and a report of detection and identification of target chemicals is provided (5) to appropriate authorities. The deconvolution method has the effect of increasing spectral resolution and separation of peaks that are not completely resolved. For example, using a simple spectral deconvolution technique, second derivative deconvolution, ion mobility spectra can be analyzed for over 75 spectral peaks whereas the number of peaks that can be analyzed without deconvolution is approximately 20 to 25. More sophisticated deconvolution techniques can increase the numbers of peaks for analysis.

When the analysis measurements or analysis spectra reveal the presence of target chemicals the identification information will be stored in memory along with date and time of the acquisition of the spectra, a report or alarm will be generated and stored in memory, and the alarm information will be transmitted to appropriate government authorities at the next inspection point in the transportation of the container. Location of the container at the time of the alarm report will be stored with the acquisition measurements or spectra and the report can be generated via satellite communications when the containers are in positions to allow such communications.

Figure 6:
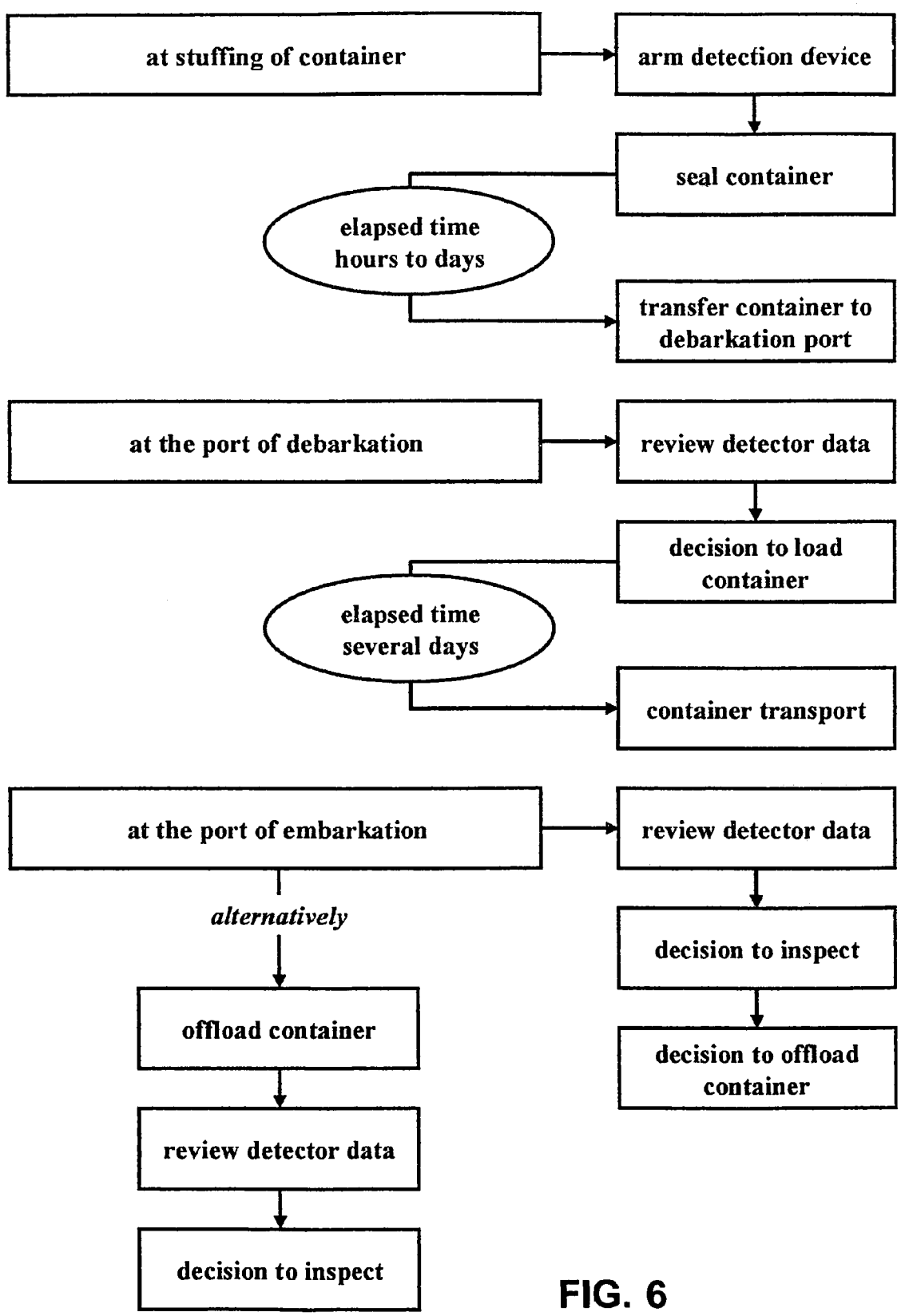
FIG. 6 is a flow diagram of a typical sequence of events in monitoring a container during transit.

A typical sequence of events is shown in the flow diagram of FIG. 6. Upon stuffing a shipping container the detection device would be armed and then the container would be sealed. Several hours to a few days could elapse before the container is ready for loading onto the shipping vessel. During the time after sealing the container and before loading it onto the shipping vessel, elapsed time of hours to days, the detection device would be interrogating the air inside the container. At the port of debarkation, the detector data would be reviewed by appropriate inspection officials and a decision could be made as to whether to load the container onto the shipping vessel. After a container is loaded onto the shipping vessel and while it is to be transported to the port of embarkation, elapsed time of several days, the detection device would be interrogating the air inside the container. At the port of embarkation, the detector data would be reviewed to determine whether to inspect the container and whether to offload the container. Alternatively, at the port of embarkation, the container could be offloaded, the detector data reviewed, and a decision whether to inspect the container could be made. Similar sequences could be used for containers transported by land, truck or rail or by air.

Many shipping containers are refrigerated for the purpose of preserving perishable goods. Such containers could be used for shipment of contraband. The internal temperature of a refrigerated container is usually much lower than the temperature of an ordinary shipping container. At lower temperatures evolution of chemical vapors from the contraband would be at a lower rate than at higher temperatures. Consequently, the concentrations of chemical vapors associated with the contraband would be at a lower concentration. In order to facilitate the chemical analysis procedure the technique known as pre-concentration could be coupled with the chemical detector. Pre-concentration involves passing a gaseous sample over or through an adsorbing media known in the art for use in adsorbing the desired molecules of interest for a period of time, typically several minutes. Alternatively, adsorption of gaseous samples on cryogenically cooled surfaces could be employed. The adsorbent material or cryogenic surface is then rapidly heated and the adsorbed chemicals are released into a chemical analysis device in a shorter period of time, typically a fraction of a second. This process has the effect of providing a sample at a significantly increased concentration to the chemical analysis device for a short period of time. Pre-concentration could be used to provide samples to a gas chromatograph coupled to an ion mobility spectrometer or other chemical detection device that would be located in the air ducts of the refrigerated container. As examples of such chemical analysis devices, combinations of adsorption and desorption air sampling systems coupled to a gas chromatograph which is coupled to an ion mobility spectrometer have been described by Genovese et al, U.S. Pat. No. 5,811,059, by Haley et al, U.S. Pat. No. 6,481,263, and by Cohen et al, U.S. Pat. No. 5,457,316. Gas chromatography—ion mobility spectrometer systems suitable for chemical analysis are commercially available but such systems that are suitable for installation and unattended operation in confined spaces of a stuffed shipping container are not known.

A device consisting of a pre-concentrator and a gas chromatograph coupled to an ion mobility spectrometer would consume electrical power at a greater rate than could be conveniently provided by normal batteries for the period of time that the container is in transit. For this reason, the chemical analysis device used to detect contraband in a refrigerated container would likely be powered from the power supply used to power the refrigeration unit of the refrigerated container.

The present invention provides a means for interfacing the analytical chemical detector to other electronic security systems such as those programmed for determinations of container breach, tracking the container and communicating contraband detection data to appropriate authorities and databases.

Using the present invention, a record of chemical detection information can be made available to aid government agencies in effecting rapid and secure flow of goods across national borders.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A method for detection and identification of illegal drugs, explosives, toxic chemicals, decaying animal and vegetable matter, and concealed human beings located in confined spaces of shipping containers, storage containers and other cargo containers and secure spaces, the method comprising the steps of:

providing an analytical chemical detector which has low power requirements and is powered by a battery to operate the detector and to sample the atmosphere within the confined spaces, disposing the analytical chemical detector in said confined spaces for a period of time wherein there is an accumulation of target chemicals associated with the illegal drugs, explosives, toxic chemicals, decaying animal and vegetable matter, and human effluvia, the analytical chemical detector being sensitive to minute concentrations of the target chemicals, providing a means for accumulating, adding and processing chemical analysis measurements periodically over said period of time as the target chemicals accumulate to significant concentrations in said confined spaces, providing digital signal processing algorithms to identify the target chemicals, providing a means for reporting the presence of the target chemicals to a device located outside of the confined spaces.

2. The method of claim 1, wherein the analytical chemical detector is an ion mobility spectrometry device.

3. The method of claim 1, wherein electronically stored libraries of target chemicals are provided to the analytical chemical detector, said libraries being compared to the samples of the atmosphere taken by the chemical agent detector.

4. The method of claim 3, wherein the libraries include data on vapors emanating from drugs and drug impurities, said vapors including precursors and solvents used during the manufacture of the drugs.

5. The method of claim 3, wherein the libraries include data on vapors emanating from explosives and impurities in explosives such as precursors, decomposition products, and chemical taggants.

6. The method of claim 3, wherein the libraries include data on vapors emanating from toxic chemical compounds used as weapons of mass destruction, chemical warfare agents, and impurities in toxic chemical compounds such as precursors and decomposition products.

7. The method of claim 3, wherein the libraries include data on vapors emanating from decaying animal and vegetable matter.

8. The method of claim 4, wherein the libraries include data on gaseous effluvia emanating from humans.

9. The method of claim 1, further providing means for interfacing the analytical chemical detector to other electronic security systems such as those programmed for determinations of container breach, tracking the container, and communicating contraband detection data to appropriate authorities and databases.

10. The method of claim 1, wherein microgram and nanogram quantities of target chemicals are detected.

11. The method of claim 1, wherein the analytical chemical detector samples the target chemicals which diffuse through the confined spaces.

12. A method for detection and identification of predetermined target chemicals in confined spaces of shipping containers, storage containers, and other cargo containers and secure spaces, the method comprising the steps of:

disposing a small, low-powered ion mobility spectrometer in the container, the spectrometer having a library of spectra of the predetermined target chemicals, obtaining an analysis spectrum of the confined spaces of the container, deconvolving the analysis spectrum and storing it in the memory of the ion mobility spectrometer during a period when the containers are in transit and awaiting distribution, comparing the deconvolved analysis spectrum with the library of the spectrometer, and providing a report of detection and identification when the deconvolved spectrum of the sampled confined spaces correspond with a spectrum in the library, the report being stored in memory and available upon request.

13. A method for detection and identification of predetermined target chemicals in confined spaces of refrigerated shipping containers, storage containers and other cargo containers in secure spaces, the method comprising the steps of:

disposing a small, low-powered ion mobility spectrometer in the refrigerated container, the spectrometer having a library of spectra of the predetermined target chemicals, pre-concentrating vapors of the target chemicals by collecting the vapors on an adsorbing media, desorbing the collected vapors of the target chemicals into the ion mobility spectrometer during a period when the containers are in transit and awaiting distribution.

comparing the analysis spectrum with the spectra in the library of the spectrometer, and providing a report of detection and identification when the spectrum of the sampled confined space corresponds with a spectrum in the library.

14. The method of claim 13, further comprising coupling a gas chromatograph with the ion mobility spectrometer.

15. The method of claim 1, wherein the analytical chemical detector is disposed in said confined space while the shipping containers and storage containers are in transit and awaiting distribution wherein the analyses occur during the dead time of the shipping process and reporting the presence of target chemicals is on demand.

* * * * *